(12) United States Patent
Tong et al.

(10) Patent No.: US 12,208,284 B2
(45) Date of Patent: Jan. 28, 2025

(54) CONTROLLER FOR RADIOTHERAPY DEVICE

(71) Applicant: ELEKTA BEIJING MEDICAL SYSTEMS CO., LTD, Beijing (CN)

(72) Inventors: Xin Tong, Beijing (CN); Andrew Jones, Beijing (CN); Tong Yang, Beijing (CN); Weicheng Zhao, Beijing (CN)

(73) Assignee: ELEKTA BEIJING MEDICAL SYSTEMS CO., LTD, Beijing (CN)

( * ) Notice: Subject to any disclaimer, the term of this patent is extended or adjusted under 35 U.S.C. 154(b) by 327 days.

(21) Appl. No.: 17/757,277

(22) PCT Filed: Nov. 26, 2020

(86) PCT No.: PCT/CN2020/131936
§ 371 (c)(1),
(2) Date: Jun. 13, 2022

(87) PCT Pub. No.: WO2021/115132
PCT Pub. Date: Jun. 17, 2021

(65) Prior Publication Data
US 2023/0001238 A1    Jan. 5, 2023

(30) Foreign Application Priority Data
Dec. 13, 2019  (CN) .......................... 201911286167.8

(51) Int. Cl.
*A61N 5/10*        (2006.01)

(52) U.S. Cl.
CPC ......... *A61N 5/1048* (2013.01); *A61N 5/1081* (2013.01); *A61N 2005/1074* (2013.01)

(58) Field of Classification Search
CPC ................ A61N 5/1048; A61N 5/1081; A61N 2005/1074
See application file for complete search history.

(56) References Cited

U.S. PATENT DOCUMENTS

| 4,866,542 A | 9/1989 | Shimada et al. |
| 6,447,451 B1 | 9/2002 | Wing et al. |
| (Continued) | | |

FOREIGN PATENT DOCUMENTS

| CN | 101247850 A | 8/2008 |
| CN | 101632590 A | 1/2010 |
| (Continued) | | |

OTHER PUBLICATIONS

"International Application Serial No. PCT/CN2020/131936, International Search Report dated Feb. 26, 2021", (Feb. 26, 2021), 4 pgs.

(Continued)

*Primary Examiner* — Nicole M Ippolito
(74) *Attorney, Agent, or Firm* — Schwegman Lundberg & Woessner, P.A.

(57) ABSTRACT

A controller (600) for a radiotherapy device (320) is provided; the radiotherapy device (320) being configured to provide therapeutic radiation to a patient (308) via a source (300) of therapeutic radiation, wherein the radiotherapy device (320) comprises a first rotatable member (304), the rotation of which can alter a physical attribute of the therapeutic radiation provided, and a patient support member (310), which is linearly moveable in at least one of a longitudinal direction and a lateral direction. The controller (600) comprises a first rotatable actuator (608) for controlling a movement of the first rotatable member (304) and a second actuator (620) for controlling a movement of the patient support member (310).

18 Claims, 6 Drawing Sheets

(56) References Cited

U.S. PATENT DOCUMENTS

| | | |
|---|---|---|
| 2008/0234855 A1 | 9/2008 | Haas et al. |
| 2009/0003975 A1 | 1/2009 | Kuduvalli et al. |
| 2009/0070935 A1 | 3/2009 | Brunker et al. |
| 2013/0329856 A1 | 12/2013 | Kuwahara et al. |
| 2018/0133508 A1 | 5/2018 | Pearce et al. |
| 2018/0236267 A1* | 8/2018 | Kuang ................ A61B 6/5235 |
| 2019/0099621 A1 | 4/2019 | Koehl et al. |

FOREIGN PATENT DOCUMENTS

| | | |
|---|---|---|
| CN | 103458967 A | 12/2013 |
| CN | 103513581 | 1/2014 |
| CN | 208399930 U | 1/2019 |
| EP | 0231659 | 8/1987 |
| JP | 2008104491 A | 5/2008 |

OTHER PUBLICATIONS

"International Application Serial No. PCT/CN2020/131936, Written Opinion dated Feb. 26, 2021", (Feb. 26, 2021), 5 pgs.

"European Application Serial No. 20898929.3, European Search Report dated Nov. 23, 2023", (Nov. 23, 2023), 14 pgs.

"Chinese Application Serial No. 201911286167.8 Office Action mailed Mar. 24, 2022", 17 pgs.

* cited by examiner

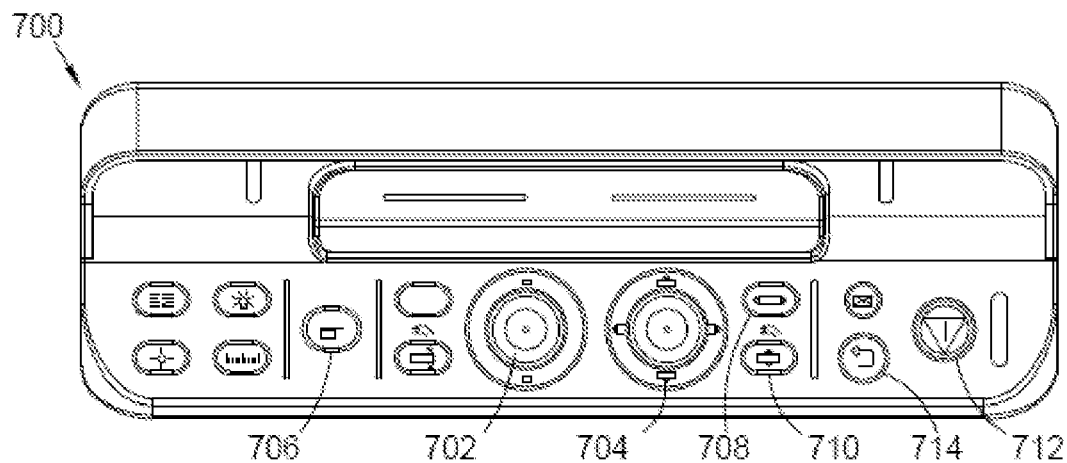
Fig.6
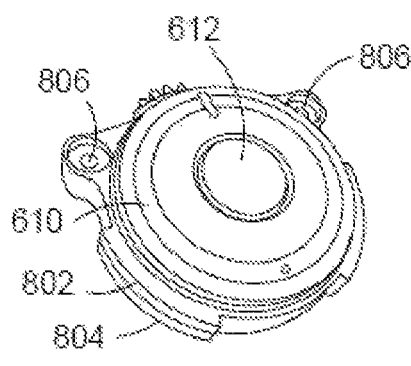 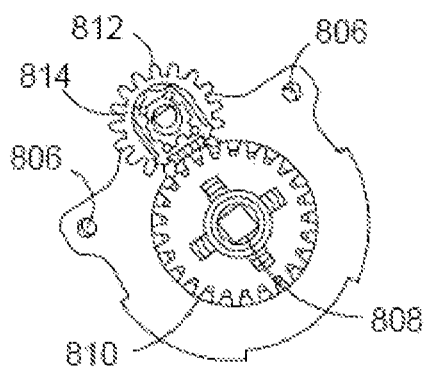
Fig.7(a)   Fig.7(b)

CONTROLLER FOR RADIOTHERAPY DEVICE

PRIORITY APPLICATIONS

This application is a U.S. National Stage Filing under 35 U.S.C. § 371 from International Application No. PCT/CN2020/131936, filed on Nov. 26, 2020, and published as WO2021/115132 on Jun. 17, 2021, which claims the benefit of priority to Chinese Application No. 201911286167.8, filed on Dec. 13, 2019; the benefit of priority of each of which is hereby claimed herein, and which applications and publication are hereby incorporated herein by reference in their entireties.

This disclosure relates to radiotherapy devices and the control of radiotherapy devices.

BACKGROUND

Radiotherapy can be described as the use of ionising radiation to treat a human or animal body. In particular, radiotherapy is commonly used to treat tumours within the body and skin of a human or animal patient. In such treatments, the cells forming part of the tumour are irradiated by ionising radiation in order to destroy or damage them. However, in order to apply a prescribed dose of ionising radiation to a target location or target region, such as a tumour, the ionising radiation will typically also pass through healthy tissue of the human or animal body. Therefore, radiotherapy has the desirable consequence of irradiating and damaging a target region, but can also have the undesirable consequence of irradiating and damaging healthy tissue. It is desirable to minimise the dose received by healthy tissue in radiotherapy treatment. It is thus desirable to control the application of the radiotherapy treatment as effectively as possible.

Modern radiotherapy treatment uses techniques to target the tumour (or other target region) as accurately as possible and to reduce the radiation dose to healthy tissue, thereby providing a safer treatment for the patient. For example, a standard approach to minimising a radiation dose received by healthy tissue surrounding a target region is to direct the radiation towards the target region from a plurality of different angles, for example by rotating a source of radiation around the patient by use of a rotating gantry. In this case, the angles at which radiation is applied are selected such that each beam of radiation passes through the target region. In this way, a cumulative radiation dose may be built up at the target region over the course of a treatment arc, in which the radiation source rotates through a certain angle. However, because the radiation is applied from a plurality of different angles, the same, high, cumulative radiation dose is not built up in any portion of the healthy tissue because the specific healthy tissue that the radiation passes through varies with angle. Therefore, each unit volume of the healthy tissue receives a smaller radiation dose, relative to a unit volume of the target region.

The effectiveness of any therapeutic radiotherapy treatment will be dependent on many contributing factors such as, but not limited to, the capabilities of the machine or device being used to apply the therapeutic radiation and the extent to which the user is able to control the operation of the device, in addition to unique factors pertaining to the individual patient and the nature of his or her tumour or other target region. The extent of user control can be dependent on the skill and experience level of the user and on the level of responsiveness of the radiotherapy device to the user's control signals.

Therapeutic radiotherapy devices are generally, by their inherent nature, complicated and sophisticated and can comprise many physical aspects including the table or other patient support surface, which usually has to be linearly moveable vertically, laterally and longitudinally, and the source of the therapeutic radiation, which also may be moveable. In some devices, there are also additional components such as imaging devices and detectors. The user of the therapeutic radiotherapy device needs to maintain good control over the various physical aspects of the device, whilst often also having to communicate with the patient and/or otherwise remain aware of the patient's needs and wellbeing.

In known therapeutic radiotherapy devices, such as known medical linear accelerator (LINAC) devices, a plurality of controllers is provided, for controlling facets of the device's operation. For example, there can be separate controllers for controlling the application of radiation, for different types of imaging and for controlling physical movement of components of the device. Each controller typically comprises a number of user-actuatable buttons or other actuators. These controllers are typically remote and can be hand held.

It is known to provide a set of LINAC controllers such as the set of controllers 100 shown in FIG. 1 herein. As shown therein, each controller in the set comprises one or more 'thumbwheels' 102 and buttons 104 or other actuators, for controlling movement of component parts of a therapeutic radiotherapy device. The 3 controllers 100 shown in FIG. 1 are all required, for use by the user, in order to provide operational control of the corresponding LINAC device. For example, the controller may control rotational movement of a rotatable frame or gantry, and/or linear movement of a table, and/or pivotal movement for folding/deploying imaging panels. In such known devices, the buttons 104 can be used to switch through different functions for the two thumbwheels, for multiple different components of the LINAC device. This system is complicated and non-intuitive for users, especially for new or infrequent users of the controllers. It relies heavily on the user reading a separate screen or screens, to ascertain what function each thumbwheel is currently switched to. Again, this is inefficient, complicated and inconvenient for the user.

The gantry (not shown in FIG. 1) can have important operational devices mounted thereon, such as the source and/or the detector of the therapeutic radiation beam. It also may have imaging equipment mounted thereon. For example, the source may be a kV source (Kilo-Volt X-Ray Generator, which is used for imaging, or an MV (MegaVolt) radiation source, which is used for therapeutic as well as imaging purposes. Known radiotherapy devices can also include other components such as the collimator, which is used for directional and shape control of the therapeutic radiation, generated within the device. The collimator forms part of a radiation source, which can be fixed to the gantry. In some arrangements, the collimator, or part of the collimator, can also be rotatable.

In the known controllers 100 of FIG. 1, the thumbwheels 102 are physically distinct to, but situated within, the main longitudinal user-input surface of the controller 100. The thumbwheels 102 in the example shown in FIG. 1 are rotatable about a longitudinal axis that runs parallel to the longitudinal axis of the controller 100. The thumbwheels 102 are generally cylindrical (wheel-shaped), and a portion of the curved face 106 of each thumbwheel 102 projects out from the plane of the user-input surface of the controller 100. The movement required, from the user, involves the user lifting his or her thumb away from the main plane of the user-input surface, to rotate the portion of the thumbwheel(s) 102 that projects outwards.

Known LINAC controllers can be hard to understand and non-intuitive to learn how to use. Also, because known Linac systems require multiple controllers, which usually look substantially identical to one another, for controlling different respective parts of the machine, there is a risk of confusion for the user. It is also time consuming for the user to repeatedly change controller and to check that the current controller is the correct one, for his or her intended purpose. This therefore runs the risk of slow operation of the corresponding therapeutic radiotherapy device, which could diminish patient experience and reduce the effectiveness of the therapeutic radiotherapy delivered.

It is desirable for the controls of a therapeutic radiotherapy device to be as user-friendly as possible, in order to: increase the effectiveness of the radiotherapy for treating the target region; avoid damage to healthy tissue that could otherwise be caused by inaccurate targeting of the radiotherapy; increase the speed of radiotherapy and improve patient throughput; improve patient experience; improve the speed and facility with which a new or infrequent user of the device can understand, learn and retain how to use it; and limit the risk of user error or inaccuracy.

SUMMARY

An improved controller for a therapeutic radiotherapy device is provided, which enables the user to control operation of the radiotherapy device, such as a medical linear accelerator (LINAC) device, efficiently and accurately. Moreover, the controller is intuitive to use, so that a new user can quickly and readily become comfortable with using it. The controller can be a handheld controller.

In contrast to known systems, in which multiple (often substantially identical) controllers were required for controlling multiple different respective aspects of operation, the improved controller described herein enables control of those multiple different aspects via a single streamlined controller module (or device). In order to achieve this, the controller embodies intelligent recognitions of, for example, which functions do not need to be used simultaneously, and of which functions, modes or facets a user might routinely wish to switch between. It also provides physically distinct areas, on the surface of the controller, with actuators for respectively controlling physically distinct components of a therapeutic radiotherapy device. Moreover, it provides user-friendly, ergonomically comfortable and efficient means for the user controlling the components of the therapeutic radiotherapy device, switching between functions or operating modes, or switching between controlling different respective facets of a radiotherapy device.

At least in some arrangements, certain controls have been omitted from the controller and have instead been relocated to the machine-based UIM (or located solely on the UIM, rather than also duplicating o the controller). Again, this comprises the embodiment of intelligent recognitions and selections about what a user needs to do, for controlling operation of a radiotherapy device, including recognition of which controls are required for initial set up and which are required during operation, when radiotherapy is being delivered to a patient.

The controller described herein also makes intelligent use of the physical space that it has available. For example, some functions that are seldom required may be provided on a rear surface of the controller.

According to an aspect, a controller for a radiotherapy device is provided; said radiotherapy device being configured to provide therapeutic radiation to a patient via a source of therapeutic radiation, wherein said radiotherapy device comprises a first rotatable member, the rotation of which can alter a physical attribute of the therapeutic radiation provided, and a patient support member, which is linearly moveable in at least one of a longitudinal direction and a lateral direction. The controller comprises a first rotatable actuator for controlling a movement of the first rotatable member and a second actuator for controlling a movement of the patient support member.

The radiotherapy device may be a therapeutic radiotherapy device.

The controller may be a moveable controller, for example a handheld controller.

The first rotatable member may be any of: a gantry, a collimator and a multi-leaf collimator (MLC). The physical attribute of the provided therapeutic radiation, which rotation of the first rotatable member can alter, may comprise one or more of: the location of the source of the therapeutic radiation; the direction in which the therapeutic radiation propagates; the cross-sectional size of a beam of the therapeutic radiation; and the cross-sectional shape of a beam of the therapeutic radiation.

The patient support member may be a patient table or patient bed or patient seat, on which a patient rests for the application of therapeutic radiation therapy.

The first rotatable actuator may be biased towards a rest position and the controller may be arranged for detection of a user actuation of the first rotatable actuator, away from its rest position. A movement of the actuator away from its rest position may be used to control a property of the movement of the first rotatable member. For example, the property of the resultant motion of the first rotatable member, which a movement of the first rotatable actuator away from its rest position can be used to control, may comprise any of: speed, velocity, and angular position.

The first rotatable actuator may comprise a dial, at least part of which is rotatably moveable. The dial may be substantially ring-shaped or annular. There may be a button or switch provided substantially at the centre of the dial.

The controller may comprise a potentiometer for conveying a control signal to the radiotherapy device, based on the movement of the first rotatable actuator away from its rest position. The controller may comprise a cog or gear or connector for conveying movement to (a part of) the potentiometer, in response to a movement of the first rotatable actuator.

The first rotatable actuator may be provided on a user input surface of the controller, and may be configured so that a user's actuation of the first rotatable actuator can be provided in substantially the same plane as the user input surface. The first rotatable actuator may be configured so that the user does not have to lift or rotate his or her thumb or finger away from the plane of the user input surface, in order to actuate the first rotatable actuator.

The controller may be configured so that the size of a movement of the first rotatable actuator away from rest position, as a result of an actuation by the user, is proportional to the size of a resultant change in the property of the movement of the first rotatable member, which is being controlled. For example, the property may be speed and the size (or extent) of the change in speed of the first rotatable member may be dependent on the size of the actuation of the first rotatable actuator away from rest position. There may be a maximum allowable speed of the first rotatable member. There may be a maximum allowable displacement of the first rotatable member, away from a reference position.

The extent to which the first rotatable actuator may be actuated, by a user, may be restricted. For example, the first rotatable actuator may be actuatable by up to 90° in both clockwise and anti-clockwise directions. For example, the first rotatable actuator may be actuatable by up to 60° in both clockwise and anti-clockwise directions.

The controller may be configured so that a direction of the movement of the first rotatable actuator, away from its rest position, as a result of an actuation by the user, will determine a direction of a resultant change in position of the first rotatable member. For example, a rotation of the first rotatable actuator in a clockwise direction, away from its rest position, may result in movement of the first rotatable member in a positive direction. For example, a rotation of the first rotatable actuator in an anti-clockwise direction, away from its rest position, may result in movement of the first rotatable member in a negative direction.

The first rotatable actuator may be spring-biased to its rest position. The first rotatable actuator may be configured to return to its rest position in the absence of a user actuation. The first rotatable actuator may comprise an indicator or indicators to inform the user of the instantaneous position of the first rotatable actuator, relative to its rest position.

The radiotherapy device further may comprise a second rotatable member. For example, the first rotatable member may comprise a gantry and the second rotatable member may comprise a collimator, or vice versa.

The controller may be arranged for selective control of movement of the first and second rotatable members, using the first rotatable actuator. Therefore, the same first rotatable actuator may be operable to control both first and second rotatable members, but not at the same time. The selective control may therefore enable the first rotatable actuator to be used to control either the first rotatable member or the second rotatable member, in accordance with a user selection. The controller may comprise a switch, button or other actuator for input of a user selection to determine which rotatable member to control, at a given time. There may be a visual indicator provided, to indicate which rotatable member is currently selected.

The second actuator, which is for controlling a movement of the linearly-moveable patient support member, may be configured to be actuated using substantially linear user movements. For example, the second actuator may comprise a 'slider' or a push-actuator. The direction in which the user pushes or slides the second actuator may control the direction in which the patient support member moves. The second actuator may be moveable in 4 directions—for example, up, down, left and right. The second actuator may be biased to a neutral position or rest position. The neutral position or rest position may be located substantially in the centre of the different directions in which the second actuator is configured to move.

The second actuator may be provided proximate to, but physically distinct from, the first rotatable actuator, on the controller. For example, the second actuator may be provided beside, or just above, or just under, the first rotatable actuator. For example, the second actuator and the first rotatable actuator may be located, on a surface of the controller, such that a typical adult user could readily switch between actuating the second actuator and actuating the first rotatable actuator, using his or her thumb, without having to move his or her hand or having to change his or her grip on the controller. For example, the distance between the first rotatable actuator and the second actuator may be between 20 mm and 70 mm. For example, the distance between the first rotatable actuator and the second actuator may be between 30 mm and 60 mm. For example, the distance between the first rotatable actuator and the second actuator may be between 40 mm and 50 mm. For example, the distance between the first rotatable actuator and the second actuator may be approximately 45 mm. This distance may be a distance between the centre of the first rotatable actuator and the centre of the second actuator. This distance may be a distance between an actuatable part of the first rotatable actuator and an actuatable part of the second actuator.

The controller may comprise a single physical entity, such as a single device, for example a single handheld device. The controller may be configured to be able to work independently and not to need to rely on any other devices, controllers or input mechanisms in order to control the first rotatable member and the patient support member of the radiotherapy device.

The controller may also be configured to control movement of other components of a radiotherapy device. For example, it may have an actuator for controlling the movement of one or more panels within a radiotherapy device. The actuator for controlling the movement of one or more panels may be physically distinct to the first rotatable actuator and the second actuator.

The controller may be configured to work—in accordance with a user preference or a user selection—in conjunction with a second input means. For example, the controller may be a moveable controller, for example a handheld controller, and the user may be able to select to also use a fixed input means on the radiotherapy device (that may be referred to as a User Interface Module TIM') for some controls of the radiotherapy device, at least at some times.

According to an aspect a radiotherapy device is provided, wherein said radiotherapy device is configured to provide therapeutic radiation to a patient via a source of therapeutic radiation, wherein said therapeutic radiotherapy device comprises a first rotatable member, the rotation of which can alter a physical attribute of the therapeutic radiation provided, and a patient support member, which is linearly moveable in at least one of a longitudinal direction and a lateral direction. Said therapeutic radiotherapy device is configured for control by a controller comprising a first rotatable actuator for controlling a movement of the first rotatable member and a second actuator for controlling a movement of the patient support member.

According to an aspect there is provided a controller for a radiotherapy device; said radiotherapy device being configured to provide therapeutic radiation to a patient via a source of therapeutic radiation, wherein said radiotherapy device comprises a first rotatable member, the rotation of which can alter a physical attribute of the therapeutic radiation provided. The controller comprises a first rotatable actuator for controlling a movement of the first rotatable member, wherein said first rotatable actuator is provided on a user input surface of the controller, and is configured so that a user's actuation of the first rotatable actuator can be provided in substantially the same plane as the user input surface.

The first rotatable actuator may be configured so that the user does not have to lift or rotate his or her thumb or finger away from the plane of the user input surface, in order to actuate the first rotatable actuator. The first rotatable actuator may have a different tactile feel to the tactile feel of an area of the user input surface that surrounds the first rotatable actuator.

According to an aspect there is provided a controller for a radiotherapy device; said radiotherapy device being configured to provide therapeutic radiation to a patient via a source of therapeutic radiation, wherein said radiotherapy device comprises a first rotatable member and a second rotatable member, wherein the rotation of each of the first rotatable member and the second rotatable member can alter a physical attribute of the therapeutic radiation provided. The controller comprises a first rotatable actuator for selectively controlling a movement of the first rotatable member and a movement of the second rotatable member.

The controller may comprise an actuator for inputting a user selection regarding which of the first rotatable member and the second rotatable member is to be controlled.

According to an aspect there is provided a controller for a radiotherapy device; said radiotherapy device being configured to provide therapeutic radiation to a patient via a source of therapeutic radiation, wherein said radiotherapy device comprises a first rotatable member, a patient support surface and a radiation panel. The controller comprises first, second and third actuators, configured to control movement of the first rotatable member, the patient support surface and the radiation panel, respectively.

According to an aspect a radiotherapy device is provided, wherein said radiotherapy device is configured to provide therapeutic radiation to a patient via a source of therapeutic radiation, wherein said therapeutic radiotherapy device is configured for control by a controller according to any of the above aspects.

According to an aspect a system is provided comprising a controller and a radiotherapy device, according to any of the above aspects.

FIGURES

Specific arrangements are described herein, by way of example only, with reference to the figures, of which:

Figure 3:
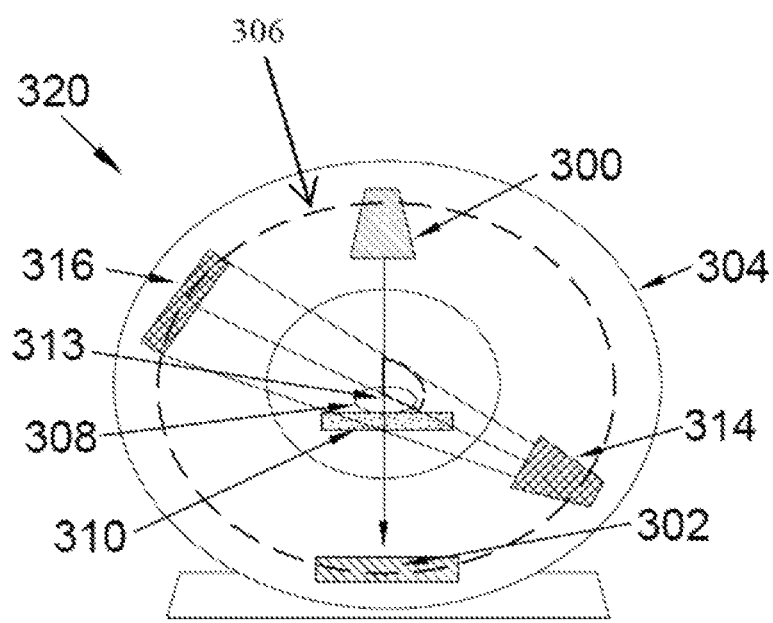
Figure 4:
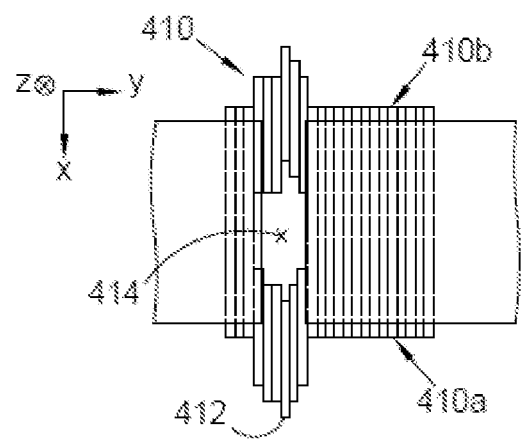
Figure 5A:
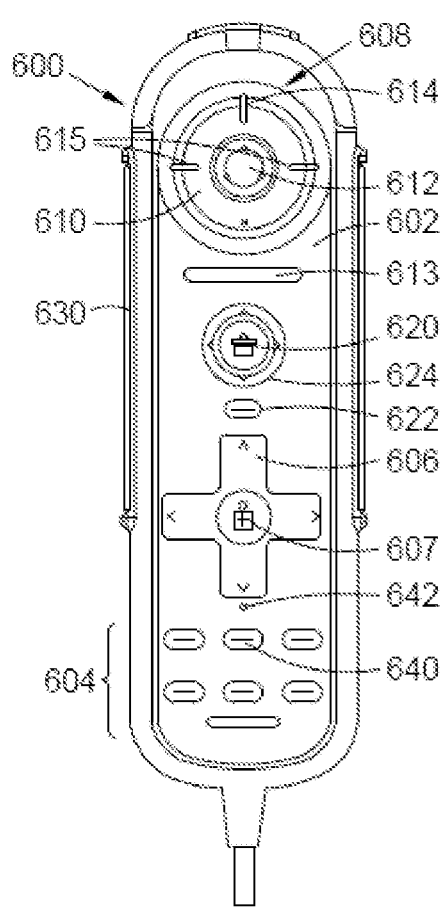
Figure 5B:
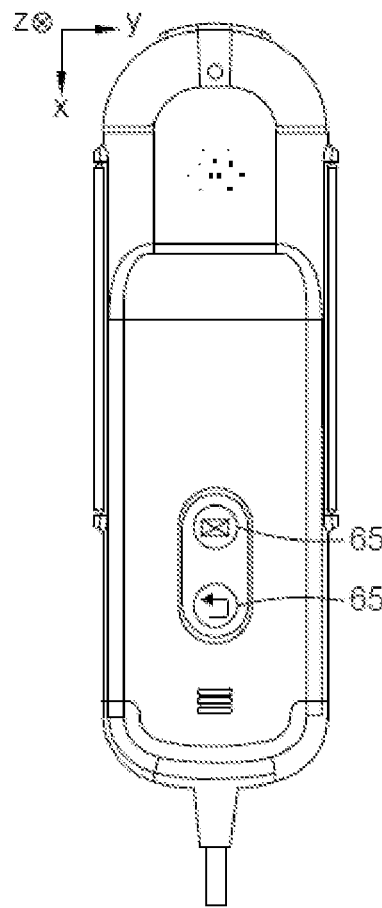
Figure 5C:
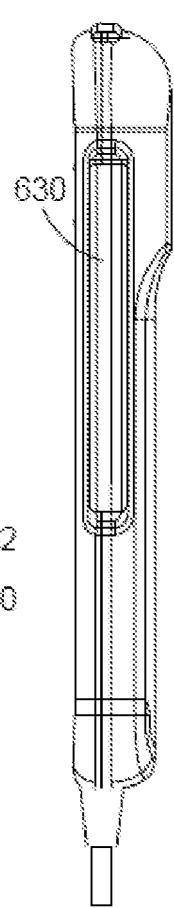
Figure 7C:
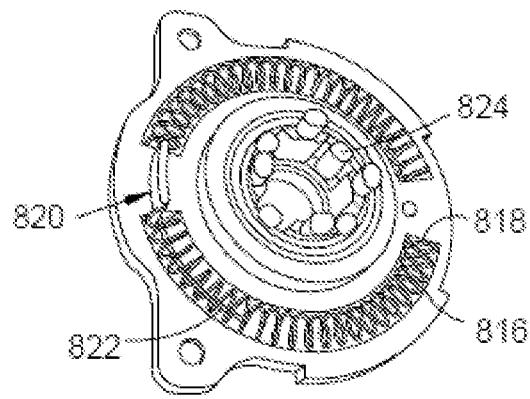
Figure 7D:
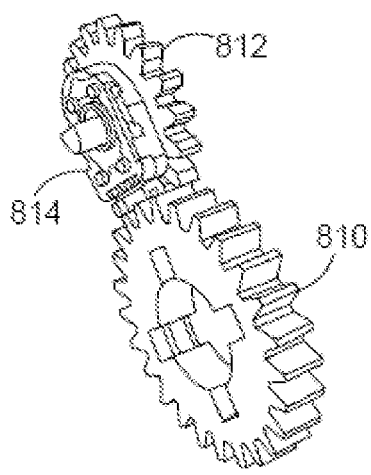
Figure 7E:
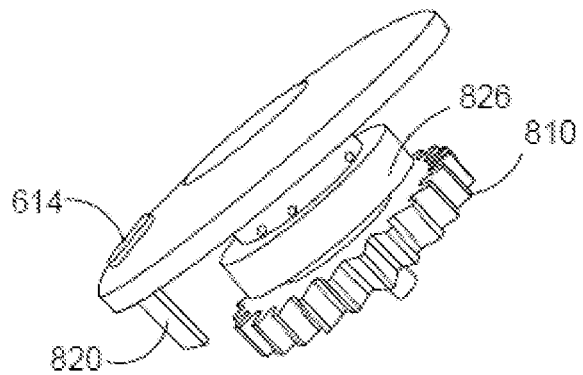

FIG. 3 shows an example LINAC device with a rotating gantry which houses a radiation source and a radiation detector and imaging equipment FIG. 4 shows a block collimator and a multi-leaf collimator for a radiotherapy head, viewed along the beam axis FIG. 5(a) shows an front view of improved controller for a therapeutic radiotherapy device FIG. 5(b) shows an rear view of improved controller for a therapeutic radiotherapy device FIG. 5(c) shows an side view of improved controller for a therapeutic radiotherapy device FIG. 6 shows an improved machine-based User Interface Module (UIM) for a therapeutic radiotherapy device FIG. 7(a) shows a front view of a dial mechanism for an improved controller;

FIG. 7(b) comprises a rear view of the dial mechanism of FIG. 7(a), without a PCB;

FIG. 7(c) comprises a rear view of the dial mechanism of FIG. 7(a), without cogs or a potentiometer;

FIG. 7(d) comprises cogs and a potentiometer for the dial mechanism of FIG. 7(a);

FIG. 7(e) comprises a side view of a dial cap, rolling bearing and first cog of the dial mechanism of FIG. 7(a).

DETAILED DESCRIPTION

High-Level Overview of a LINAC Radiotherapy Device

Figure 1:
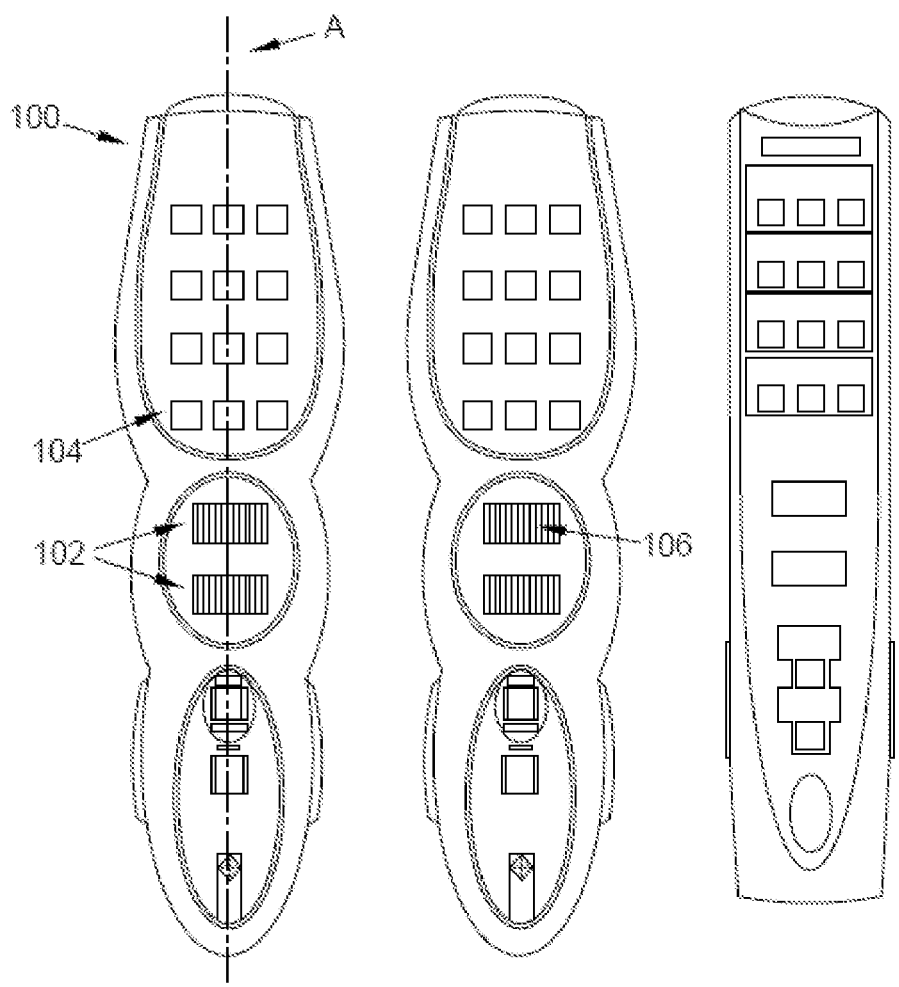
FIG. 1 shows a known set of LINAC controllers
Figure 2:
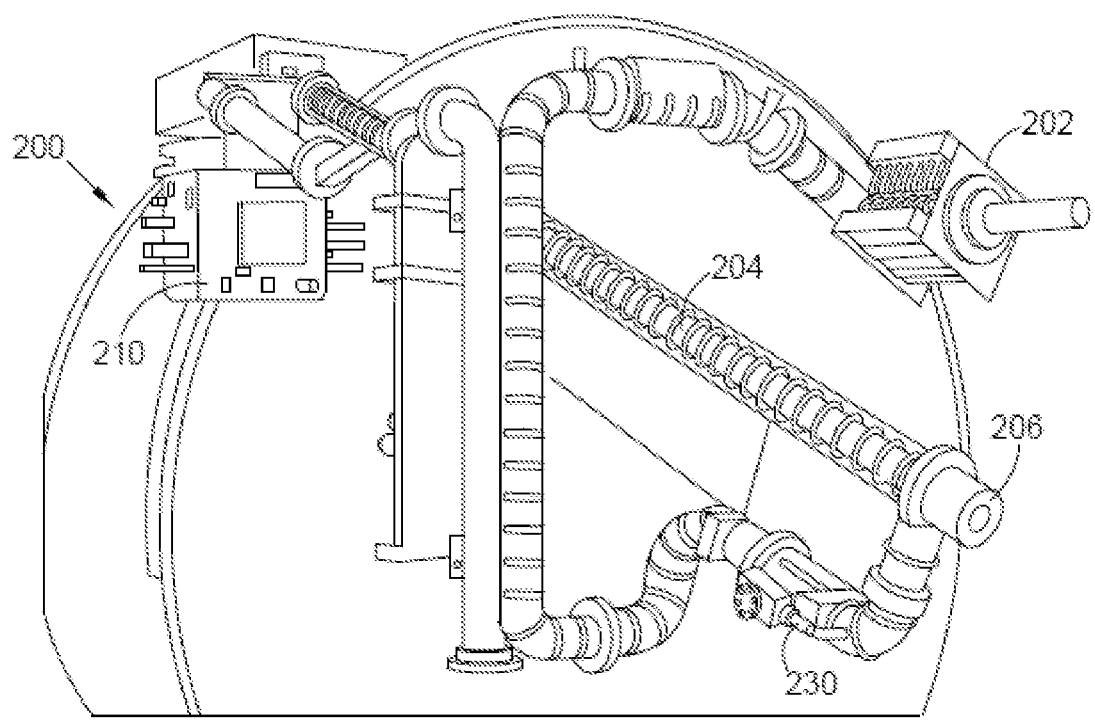
FIG. 2 shows an example Linear Accelerator (LINAC) device.

FIG. 2 shows a known LINAC 200, suitable for delivering, and configured to deliver, a beam of radiation to a patient during radiotherapy treatment. In operation, the LINAC device 200 produces, modulate and shapes a beam of radiation and directs it toward a target region within the patient's body or skin in accordance with a radiotherapy treatment plan.

A medical LINAC machine is by necessity complex, with many inter-operating component parts. A brief summary of the operation of a typical LINAC will be given with respect to the LINAC device 200 showed in FIG. 2 which comprises a source of radiofrequency waves 202, a waveguide 204, a source of electrons 206, a system capable of creating a strong vacuum comprising one or more vacuum pumps 230, a heavy metal target which produces X-rays when hit by an electron beam, and a complex arrangement of magnets capable of re-directing and focusing the electron beam onto the target. The device 200 depicted in FIG. 2 also comprises a treatment head which houses various apparatus configured to, for example, collimate and shape the resultant X-ray beam.

The source 202 of radiofrequency waves, such as a magnetron, produces radiofrequency waves. The source 202 of radiofrequency waves is coupled to the waveguide 204, and is configured to pulse radiofrequency waves into the waveguide 204. Radiofrequency waves pass from the source 202 of radiofrequency waves through an RF input window and into a RF input connecting pipe or tube. A source 206 of electrons, such as an electron gun, is coupled to the waveguide 204 and is configured to inject electrons into the waveguide 204. In the source 206 of electrons, electrons are thermionically emitted from a cathode filament as the filament is heated. The temperature of the filament controls the number of electrons injected. The injection of electrons into the waveguide 204 is synchronised with the pumping of the radiofrequency waves into the waveguide 204. The design and operation of the radiofrequency wave source 202, electron source 206 and the waveguide 204 is such that the radiofrequency (RF) waves accelerate the electrons to very high energies as they propagate through the waveguide 204. The design of the waveguide 204 depends on whether the LINAC 200 accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 204.

As the electrons are accelerated in the waveguide 204, the electron beam path is controlled by a suitable arrangement of steering magnets, or steering coils, which surround the waveguide 204. The arrangement of steering magnets may comprise, for example, two sets of quadrupole magnets.

Once the electrons have been accelerated, they pass into a flight tube. The flight tube may be connected to the waveguide 204 by a connecting tube. This connecting tube or connecting structure may be called a drift tube. The drift tube also forms part of a vacuum tube. RF waves exit the waveguide 204 via an RF output connecting pipe or tube coupled with the drift tube. As with the RF input pipe which introduces RF to the waveguide 204, the pipe or tube through which RF exits the waveguide 204 connects to the vacuum tube via an elbow joint or 'T-shaped' joint. RF passes out from the vacuum system via an RF output window which seals the vacuum system.

The flight tube is kept under vacuum conditions by the pump system. The electrons travel along a slalom path toward the heavy metal target. The target may comprise, for example, tungsten. Whilst the electrons travel through the flight tube, an arrangement of focusing magnets act to direct and focus the beam on the target. The slalom path allows the overall external length of the LINAC 200 to be reduced while ensuring that the beam of accelerated electrons, which is comprised of electrons with a small spread of energies, is focused on the target.

To ensure that propagation of the electrons is not impeded as the electron beam travels toward the target, the waveguide 204 is evacuated using a vacuum system comprising a vacuum pump 230 or an arrangement of vacuum pumps. The pump system is capable of producing ultra-high vacuum (UHV) conditions in the waveguide 204 and in the flight tube. The vacuum system also ensures UHV conditions in the electron gun. Electrons can be accelerated to speeds approaching the speed of light in the evacuated waveguide 204.

Together, the electron gun 206, waveguide 204 and the flight tube form a vacuum tube in which electrons can be accelerated and directed toward a target in vacuum conditions. In implementations comprising a drift tube connecting the waveguide 204 to the flight tube, the drift tube also forms part of the vacuum tube. To produce the necessary high vacuum conditions, the vacuum system may undergo several stages of pumping before a high quality vacuum may be maintained using e.g. ion pumps. For example, first, a normal piston-based pump may be used, followed by a stage wherein the pressure inside the vacuum system is further lowered using a turbo-molecular pump. Finally, ion pumps are used to ensure the system is kept at ultra-low pressure.

When the high energy electrons hit the target, X-rays are produced in a variety of directions. The target is located inside the flight tube, and is located at the end of the flight tube to seal the vacuum system. The flight tube also comprises a target window, which is transparent to X-rays, which is positioned to allow the X-rays which are produced when the LINAC 200 is in operation to pass from the evacuated flight tube through the target window and into the treatment head 210. At this point, a primary collimator blocks X-rays travelling in certain directions and passes only forward travelling X-rays to produce a cone shaped beam. The X-rays are filtered, and then pass through one or more ion chambers for dose measuring. The beam can be shaped in various ways by beam-shaping apparatus, for example by using a multi-leaf collimator, before it passes into the patient as part of radiotherapy treatment.

In some implementations, the LINAC 200 is configured to emit either an X-ray beam or an electron particle beam. Such implementations allow the device to provide electron beam therapy, i.e. a type of external beam therapy where electrons, rather than X-rays, are directed toward the target region. In such implementations, it is possible to 'swap' between a first mode in which X-rays are emitted and a second mode in which electrons are emitted by adjusting the components of the LINAC. In essence, it is possible to swap between the first and second mode by moving the heavy metal target in or out of the electron beam path and replacing it with a so-called 'electron window'. The electron window is substantially transparent to electrons and allows electrons to exit the flight tube.

The end of the flight tube may be sealed by a component which comprises both a target and an electron window. It is then possible to swap between the first and second mode by moving the flight tube such that the electron beam points toward either the target or the electron window. The drift tube, which connects the waveguide to the start of the flight tube, is therefore slightly flexible to allow the flight tube to move. In other words, the flight tube will move when the user changes between using an electron and XRay energy, this puts either the tungsten target (XRAY) or electron window (Electron) in position to treat.

A typical LINAC device such as the device 200 shown in FIG. 2 also comprises several other components and systems. The whole system is cooled by a water cooling system (not shown in the figures). The water cooling system may be used, in particular, to cool the waveguide 204, target, and radiofrequency source 202. In order to ensure the LINAC does not leak radiation, appropriate shielding is also provided. As will be understood by the person skilled in the art, a LINAC device used for radiotherapy treatment will have additional apparatus such as a gantry to support and rotate the LINAC, a patient support surface, and a controller or processor configured to control the LINAC.

The present application relates, in particular though not exclusively, to a controller that is configured to control a LINAC device or devices. In particular it relates to the control of rotatably moveable parts of a LINAC device such as a rotatable gantry and/or a rotatable beam collimator, as discussed further below.

Rotatable Gantry

FIG. 3 shows a cross section through a co-planar LINAC radiotherapy device 320 configured to provide co-planar radiotherapy treatment. A patient 308 is shown located on a table or other support surface 310, within the central part of the device 320.

The device 320 comprises a rotatable housing or gantry 304. The gantry 304 is generally rotatable about the centrepoint of the depicted cross-section—i.e. the gantry's 304 axis of rotation is generally perpendicular to the plane of the depicted cross-section. The gantry 304 has a therapeutic radiation source 300 mounted thereon and a therapeutic radiation detector 302. In the arrangement shown, the therapeutic radiation detector 302 is mounted substantially diametrically opposite the therapeutic radiation source 300, on a circular support track 306 of the gantry 304. Therefore rotation of the gantry 304 causes rotation of the therapeutic radiation source 300 and of the detector 302, in this arrangement. Moreover, the detector 302 and the therapeutic radiation source 300 are arranged to rotate together around the circular support track 306, such that they are always arranged substantially 180 degrees from one another (i.e. diametrically opposite one another) around the gantry 304. In this arrangement, there is also an imaging radiation source 314 and an imaging radiation detector 316, arranged substantially diametrically opposite one another on the gantry 304.

The therapeutic radiation source 300 is arranged to emit a targeted X-ray beam, directed towards a tumour or other target area within the patient's body or on a patient's skin. The therapeutic radiation detector 302 is arranged to detect the beam, once it has passed through the patient's body. The directionality of the beam is controlled, at least in part, by one or more collimators, which are discussed below.

In operation of the LINAC 320, therapeutic radiation is emitted in the plane of the depicted cross section, i.e. perpendicular to the axis of rotation of the therapeutic radiation source 300, therapeutic radiation detector 302 and gantry 304. Radiation can thus be delivered to a radiation isocentre 313 at the centrepoint of the gantry 304, regardless of the angle to which the therapeutic radiation source 300 is rotated. This therefore enables the therapeutic radiation source 300 to direct radiation towards a tumour or other target area within or on the patient 108, from various different angles around the patient 108. As discussed above, this is an important feature of any therapeutic radiotherapy device, to ensure that the radiation does not have to repeatedly pass through the same portion of healthy tissue within the patient, in order to reach the target area. Instead, the therapeutic radiation source 300 can be rotated to different rotational angles, so that the radiation beam passes through multiple different healthy areas, each for a limited time period, during the therapeutic radiotherapy treatment of the tumour or other target area.

Collimation of the Beam

In order to target a tumour or other target area and reduce the exposure of healthy tissue to radiation, it is important to locate the patient correctly within a therapeutic radiotherapy device, so that the target area is at the radiation isocentre 313. Thus, the table or other support surface 308 on which the patient is located is usually linearly moveable both vertically and horizontally. In some arrangements, the table is also rotatable along the vertical axis through the radiation isocentre (i.e. rotatable about the Z-axis) for non-coplanar treatment. Moreover, in order to successfully target the tumour or other target area, the shape of the radiation beam should be arrangeable to fit the shape, size and nature of the tumour, as closely as possible.

Most tumours can be targeted using a combination of block collimators and a so-called "multi-leaf" collimators (MLC's). A block collimator is usually a solid block of radiopaque material such as tungsten, which usually has a straight front edge that spans the entire width of an aperture, from which the radiation beam is emitted, and which can be advanced and/or withdrawn across the aperture in a direction transverse to the front edge. Thus, the block collimator has the effect of adjusting the width of the aperture as needed. A pair of such collimators arranged face-to-face can thus narrow the aperture from both opposing sides. A multi-leaf collimator (MLC) comprises an array of long, narrow, deep leaves' of radiopaque material that, in some arrangements, can each be extended into and out of the aperture. Arranged side-by-side in an array; the tips of the leaves therefore define a chosen shape which can be varied at will by extending or retracting individual leaves.

FIG. 4 shows a view along the beam axis of a known collimation arrangement. The purpose of the collimators is to allow the transmission of a beam which has a desired cross-section and to provide as complete shielding as possible across the remainder of the beam field (i.e. the maximum extent of the beam). To allow shaping of the beam, a multi-leaf collimator (MLC) 410 is provided which comprises a series of individual leaves 412 of a radiopaque material such as tungsten, arranged side-by-side relative to each other, in two opposing arrays 410a, 410b. Thus, the lower array 410a extends into the beam field in the x direction from one side of the field, and the upper array 410b extends into the beam field in the x direction from the opposing side of the field. Each leaf 412 can each be moved independently of the others so as to define a chosen shape 414 between the tips of the opposing leaf banks 410a, 410b. Each leaf is thin in its transverse (y) direction to provide good resolution, is deep in the (z) direction to provide adequate absorption, and long in its longitudinal (x) direction to allow it to extend across the field to a desired position. Generally, the longitudinal length of the leaf will be greater than its depth, and both will be much greater than its transverse thickness.

According to an arrangement described herein, the control of which is described further below, the collimator is provided on or within a radiation head (such as the therapeutic radiation source 300 described above in relation to FIG. 3a), which is attached to a rotatable gantry of a LINAC device. The therapeutic radiation beam from the radiation head is directed towards the isocentre of gantry rotation and the collimator delimits the beam to a desired beam shape. The collimator may include a block collimator. In this arrangement, it comprises an MLC such as the one shown in FIG. 4 which has two opposing banks or arrays of leaves, each leaf being moveable in one direction to delimit the beam into a desired shape of e.g. a tumour or other target area.

In the example shown in FIG. 4 each leaf 412 is laterally moveable in the x direction only. The extent to which the MLC can achieve different beam shapes is therefore limited. According to an arrangement, in order to enhance the extent to which the MLC can achieve different beam shapes, the MLC is also rotatable about the beam propagation axis (shown as the y axis in FIG. 4.) Rotating the MLC rotates the rotational angle of the leaves and thus enables the MLC to achieve a greater number of different beam shapes. It therefore enhances the bespoke targeting of tumours or other target areas, that is achievable by the LINAC device.

Control of a Therapeutic Radiotherapy Device

An improved controller for controlling a therapeutic radiotherapy device, such as a LINAC device, according to an arrangement described herein, is provided, as shown in FIG. 5, which comprises FIGS. 5(a), 5(b) and 5(c). The controller 600 in this arrangement acts as a single controller that is operable to control operation of a LINAC device (not shown in FIG. 5), either independently or in conjunction with a machine-based User Interface Module (UIM) that is also described further below. The controller 600 can therefore replace the multiple handheld controllers that known LINAC systems typically require.

The controller 600 embodies intelligent recognition of which functions are required by a user, in order to control operation of a LINAC device. This includes recognition of which functional features are typically used at mutually-exclusive times, which features are typically used at similar times and which patterns of movement and control are natural and intuitive for a user to make, when using a handheld device. The controller 600 is sized so as to be handheld by the user. In fact, the controller 600 is particularly compact and user-friendly and, at least in the particular arrangement described in relation to FIG. 5 herein, is generally smaller than the handheld controllers of known LINAC devices.

Looking first at FIG. 5(a), which shows a front view of the controller 600, it can be seen that the controller 600 in this arrangement has a substantially rectangular profile, with rounded corners for improved ergonomic feel and comfort. The front elongate face, which is to be held facing the user's line of sight when the controller 600 is in use, comprises a user input surface 602. The user can provide input to the controller 600 via various features on the user input surface 602, in order to control aspects of the corresponding therapeutic radiotherapy device's operation.

In the arrangement of FIG. 5, the controller 600 comprises, provided on the user input surface 602, a number of user-depressible buttons 604, which enable the user to make selections. It also comprises a substantially cross-shaped actuator 606, wherein the ends of each of the four branches of the cross-shaped actuator 606 can be depressed by the user. Also provided on the user input surface 602 is a user-actuatable dial 608. This dial 608 can be used to control movement of rotatable components of a therapeutic radiotherapy device, with continuously variable speed, as will be discussed further below. The user input surface 602 also comprises a separate 'table controller' actuator 620 that can be used to control movements of the patient table within a therapeutic radiotherapy device, as will also be discussed further below.

The user-actuatable dial 608 (also referred to herein as a so-called 'thumb dial' 608) is substantially circular, with an outer ring 610 and an inner, substantially circular button 612, located within the outer ring 610. The inner substantially circular button 612 comprises a 'thumb dial function selector' 612, as discussed further below. The surface of the dial 608, via which the user can input control signals to the therapeutic radiotherapy device, is generally co-planar or 'flush' with the user-input surface 602 of the controller 600. However the surface of the dial 608 can be slightly raised or lowered with respect to its surrounding area(s) on the user-input surface 602, in order to provide improved tactile feedback to the user regarding the location of the dial 608 and to prevent the dial 608 from being accidentally actuated when the user does not intend to actuate it. Alternatively or additionally, the surface material of the dial 608, and in particular of the outer ring 610, can have a different material feel to some or all of the other parts of the user-input surface 602, in order to increase tactile user feedback, and in order to provide improved user grip on the surface of the dial, for enhanced control. For example, the outer ring 610 may be formed from the same material as the rest of the user-input surface 602, but may be configured to have a different tactile feel, to the user's touch.

The dial 608 includes an upper position marker 614 located on the outer ring 610. The upper position marker 614 is provided substantially at 12 o'clock (or 0 degrees) on the outer ring 610. The upper position marker 614 is shown in FIG. 5 as a raised notch on the surface of the outer ring 610, but it could be any suitable type of position marker, which can provide visual and/or tactile feedback to the user, regarding its instantaneous position. It is helpful for the upper position marker 614 to provide both visual and tactile feedback to the user, regarding its position. It can also be helpful for the position marker 614 to be raised, to enable the user to effectively push the marker 614 with his or her finger or thumb, to move the outer ring 610 and thereby provide control input to the dial 608.

In the arrangement shown in FIG. 5, there are also two side position markers 615, located at 3 o'clock and 9 o'clock (or 90 degrees and 270 degrees) on the outer ring 610, respectively. These can be physically similar to the upper position marker 614, discussed above, and serve a similar purpose.

The dial 608 is arranged for the outer ring 610 to be rotatable by the user. The outer ring 610 is rotatable about its central axis, which extends perpendicular to the plane of the user-input surface 602 (i.e. about the z axis as shown in FIG. 5.) Therefore the outer ring 610 rotates substantially within the plane of the user-input surface 602 of the controller 600. In the arrangement shown, the upper position marker 614 is located, when the dial is in a resting position and is not being rotated by the user, at the '12 o'clock' or 0° position. As shown in FIG. 5 herein, the outer ring 610 is rotatable at least to the extent that the marker 614 can move a one-sixth turn to each of the left and the right (i.e. clockwise and anti-clockwise, from 10 o'clock to 2 o'clock, −60° to +60°.) A physical limiter (not shown in FIG. 5) is provided underneath the surface of the dial 608, in order to limit the rotation.

In principle, the user can rotate the dial 608 by having their finger(s) or thumb on any part of the outer ring 610, but many users will prefer to have their finger(s) or thumb on one of the position markers 614, 615 (particularly if it is a raised marker such as those shown in FIG. 5) and to impart the rotary controls via movement of the markers 614, 615. Because the dial 608 is substantially flush with the plane of the user-input surface 602 of the controller 600, the user's movements to actuate the dial are substantially within that plane. The user does not need to lift his or her thumb in order to actuate the dial. Therefore the user movement's required for actuating the dial are intuitive and comfortable. This is advantageous, especially for users who user the controller 600 repeatedly and/or for long periods of time, during their working day.

The marker positions inform the user of the dial's instantaneous position, relative to its zero or resting position. As detailed below, during operation of the controller 600, the rotation of the dial 608 can be used to selectively determine the speed of rotation of the gantry and of the collimator of the corresponding LINAC device, wherein (generally speaking), the greater the size of the actuation, the greater the so-called 'dialling angle' of the dial 608, and therefore the greater the speed of the component under control. The rotation speed increases when the dial is pushed away from its neutral position. The rotation speed decreases when the dial is pushed towards the neutral position. The mapping of the rotation angle of the dial 608 to the speed of movement of the selected component is not a straight line but a curve. That is; the increment of speed is smooth at the beginning of the dial's rotation and then becomes more stiff when approaching the end)(±60°. If the dial is released, at any time, it is spring-biased to return to its neutral/zero position. When the dial returns to its neutral/zero position, movement of the selected component stops immediately.

In addition to the size of the actuation of the dial 608 controlling the speed of rotation of the selected component of the LINAC device, the direction of the actuation of the dial also controls the direction in which the selected component will rotate. That is; if the dial 608 is actuated in a clockwise direction, away from its neutral position, the selected component will rotate in a positive direction, up to 180 degrees from its starting position. Conversely, if the dial 608 is actuated in an anti-clockwise direction, away from its neutral position, the selected component will rotate in a negative direction, up to 180 degrees from its starting position. The speed at which the selected component rotates will be governed by the size of the angle to which the dial is rotated, in the relevant direction. The angular extent to which the selected component will rotate, in response to an actuation of the dial 608, will depend on the speed of rotation and on the length of time for which the actuation occurs.

In order for user-input on the dial 608 to be translated into motion control of the gantry and/or collimator, the controller 600 includes a potentiometer. The basic operation of a potentiometer is well known and so is not described in detail herein. Very briefly; a potentiometer comprises an adjustable voltage divider, which typically has a resistive element with end terminals on each end—which, in this case, connect to other control circuitry within the controller— and a sliding contact which moves along the resistive element, making good contact with one point on the resistive element. The sliding contact is connected to a third terminal, housed between the two end terminals. Movement of the sliding contact—in this case, in an arc about the resistive element—changes the output voltage of the potentiometer, in accordance with the position of the sliding contact.

In the controller 600 described herein, the dial 608 connects to the potentiometer such that the position of the potentiometer's sliding contact, and therefore the output of the potentiometer, is changed by changing the angular position of the dial 608. The user can therefore use the dial 608, making adjustments relative to the neutral/zero position to which the dial 608 is biased to return, in order to change the output of the potentiometer. The control circuitry within the controller 600 can use the output of the potentiometer to convey a corresponding control signal to the LINAC device.

In this arrangement, the controller 600 has a safety feature comprising a so-called 'enable bar' 630. The enable bar 630 in fact comprises (in this arrangement) two buttons—one provided on the left side face of the controller 600 and the other provided on the right side face of the controller 600. Both enable bar buttons 630 comprise elongate substantially rectangular depressible buttons. Because the enable bar buttons 630 are provided on both sides of the controller 600, they are easy for the user to actuate, regardless of which hand he or she is holding the controller 600 in. The enable bar buttons 630 provide a safety feature because, in order to authorise the dial 608 to control gantry and/or collimator movement, as discussed above, the user must press or squeeze the enable bar (one or both buttons) 630 at the same time as actuating the dial 608. If the enable bar button(s) 630 is/are released, the selected component of the LINAC will immediately stop moving, even if the dial 608 is currently at a non-zero rotational position. The enable bar 630 therefore provides a safety backstop, against possible unintentional movement of the LINAC components, in the event that the user accidentally moves the dial 609 when he or she does not intend to do so. The enable bar also authorises the movements to be initiated and maintained by other moveable components of the Linac such the patient table and the panels, in accordance with current regulatory requirements.

According to the arrangement of FIG. 5, the dial 608 can be used to selectively control both the gantry and the collimator (or so-called 'Beam Limiting Device' BLD), wherein the user inputs a selection to the controller 600, to determine which of those two components is to be controlled at a given time. As mentioned above, the table is controlled separately, as detailed further below. The user's selection of whether to actuate the gantry or the collimator is input, in this arrangement, via the thumb dial function selector 612. The thumb dial function selector 612 is a depressible button, provided in the centre of the dial 608, which in use the user can press with any digit but he or she is likely to depress it using his or her thumb. Therefore the user does not need to move his or her hand in order to both select which component to control and subsequently to control its rotation, using the improved controller 600. The thumb dial function selector 612 enables the user to scroll through 3 different options, in this arrangement: gantry rotation, Linac ASU (Automatic Setup) and collimator rotation. Linac Automatic Setup (ASU) triggers movement of the gantry and the collimator to a pre-determined set of positions, which have been programmed (into a suitable controller within or associated with the Linac) on a patient-specific basis.

The default option for the dial 608 in this arrangement is control of gantry rotation, but the thumb dial function selector 612 can be pressed (in this case) once to change to Linac ASU and a further time to change to collimator rotation (and another time to return to gantry rotation). It is configured to make a noise such as an audible 'beep' when the thumb dial function selector 612 is pressed. In addition, there is a thumb dial function indicator 613, comprising three LED portions corresponding to the gantry, Linac ASU and collimator respectively, wherein one of the three LED portions of the thumb dial function indicator 613 is illuminated to indicate which option has been selected by the thumb dial function selector 612 at a given time.

Thus, it can be seen that the provision of the thumb dial function selector 612 provides a neat, intelligent and user-friendly way in which space is saved on the surface of the controller 600, by enabling the gantry and collimator of the Linac, and the activation of Linac ASU, all to be controlled via a single, relatively small region of the controller (comprising the dial 608 and the thumb dial function selector 612). The user is prevented from accidentally rotating the wrong Linac component, via the LED's on the thumb dial function indicator 613. Moreover, the user is prevented from accidentally rotating a component by inadvertently touch the dial 608 when he or she does not intend do, via the requirement for the enable bar 630 to also be depressed, in order for the dial 608 to cause the Linac component(s) to rotate, or to revert to their Automatic Setup (ASU) positions.

The controller 600 in this arrangement also comprises a table controller 620 for controlling movement of the table (not shown) on which the patient is positioned, within the Linac. The table controller 620 is physically distinct to the dial 608—in this arrangement, it is provided just below the dial 608, on the surface of the controller 600. So, very little user movement is required to switch between controlling the rotatable components and controlling the table movement. In this arrangement, the table controller 620 is located so that its centre is approximately 45 mm below the centre of the dial 608, on the surface of the controller 600. However in other arrangements this distance may be different—for example the respective centres (or the respective actuatable parts) of the dial 608 and the table controller 620 may be between 20 mm and 70 mm apart, or between 30 mm and 60 mm apart or between 40 mm and 50 mm apart.

The table controller 620 can control both vertical and horizontal movement of the table. There is a table movement mode selector 622 provided just below the table controller 620, wherein the table movement mode selector 622 is a depressible button that can be pressed to switch between vertical movement mode (which is the default position) to horizontal movement mode. When the horizontal movement mode has been selected, a 'table horizontal movement mode indicator' 624, which in this arrangement comprises a substantially circular backlight surrounding the table controller 620, is illuminated. When the vertical movement mode has been selected (or defaulted to), the table horizontal movement mode indicator 624 is not illuminated.

The table controller 620 in this arrangement comprises a so-called '4-way slider' with continuous variable speed and a default neutral position. When vertical table movement is selected, pushing the slider up (towards the top of the elongate user input surface 602 of the controller 600), causes the table to move upwards (i.e. in the + direction along the z axis), and pushing the slider down (towards the bottom of the elongate user input surface 602 of the controller 600), causes the table to move downwards (i.e. in the − direction along the z axis). When horizontal table movement is selected, pushing the slider up causes the table to move in the +y direction in an x-y plane, whereas pushing the slider down causes the table to move in the −y direction in the x-y plane. When horizontal table movement is selected, pushing the slider to the right causes the table to move in the +x direction in an x-y plane, whereas pushing the slider to the left causes the table to move in the −x direction in the x-y plane.

As with the dial 608, there is a safety mechanism associated with the table controller 620 in this arrangement, wherein actuating the table controller 620 will only give rise to movement of the table if one or both of the enable bar buttons 630 is also depressed at the same time. Releasing the table controller 620 to its neutral position and/or releasing the enable bar button(s) 630 will cause immediate cessation of the table movement, in this arrangement. The extent to which the table controller 620 is pushed in a selected direction will determine the speed at which the table moves, in the corresponding direction, wherein the speed increases as the table controller slider moves further from its neutral position, and decreases as it nears its neutral position The user is provided with one or more screens (not shown in the figures) that can provide geometric readings relating to table/gantry/collimator positions.

The controller 600 also comprises panel shift controls which, in this arrangement, are physically distinct to both the dial 608 and the table controller 620 and comprise a cross-shaped actuator 606 and a substantially circular panel centring button 607, provided in the middle of the cross-shaped actuator 606. There are two panels (neither shown in FIG. 5) in the Linac, which can be controlled by the panel shift controls. As will be known to the skilled reader; both panels are configured to detect X-rays but at different respective energy levels—one is configured for kV detection and the other is configured for MV. The default panel is a kV panel (also referred to in this arrangement as an 'XVI' panel). The other panel is an MV panel (also referred to in this arrangement as an 'iView' panel). There is a depressible iView (MV) mode button 640, provided substantially below the cross-shaped actuator 606, which can be pressed to change control from the kV panel to the MV panel. There is an iView (MV) panel mode indicator 642 which illuminates when the MV panel has been selected for control.

The panel centring button 607 can be depressed, for the selected panel, in order for it to move to its centralised position. The cross-shaped actuator can then be used to move the selected panel in the x and y directions, both positively and negatively with respect to centre (i.e. up and down, left and right) by depressing the corresponding branch of the cross. The panels are configured to move to a maximum/limit position, in the corresponding direction, when the respective branch of the cross-shaped actuator 606 has been pressed.

The enable bar 630 also acts as a safety mechanism with respect to panel movement, wherein the panel shift controls will only impart movement to the panel(s) if the enable bar button(s) is/are also depressed at the same time as the panel shift controls are actuated.

The controller 600 also comprises some additional buttons in this arrangement, shown general in the lower region 604 in FIG. 5. For example, the buttons may include controls for activating a room light for the room in which the Linac is situated, for activating a torch within the controller, for activating a laser beam for marking a target region for the therapeutic radiation to be applied to, and so on. There is also an LED bar towards the bottom of the user input face 602, which is illuminated when the controller 600 is switched on.

As shown in FIG. 5(b), there are also some actuators on the rear face of the controller 600 in this arrangement. These include a 'reset motors' button and a 'touchguard override' button 652, which can be used in conjunction with the enable bar 630 to override any pre-set inhibits or limits that have been put in place in relation to any of the moving parts of the Linac. It can be seen that these two actuators are intelligently placed on the rear surface of the controller 600 since they are likely to be used very infrequently.

Turning again to the functionality of the dial 608; FIG. 7(a) herein shows the dial 608 in isolation, not in situ within the controller 600. In addition to the outer ring 610 and the depressible thumb dial function selector 612, the dial mechanism comprises an upper housing 802 and a lower housing 804 and screw holes 806 for attaching it into the body of the controller 600.

Looking at FIG. 7(b); it can be seen that the rear side of the dial 608 comprises a first cog 810 and a second cog 812. The first cog 810 is actuated via the user actuating the outer ring 610, on the front surface of the dial 608. Movement of the first cog 810 drives the second cog 812, to which the potentiometer 814 connects. There is also a microswitch 808 substantially at the centre of the rear view of the dial 608, which is actuated via the user depressing the thumb dial function selector 612 on the front surface of the dial 608. The microswitch 808 connects to a PCB (not shown) in order to convey control signals when the thumb dial function selector 612 is pressed.

FIG. 7(c) is a rear view of the dial 608 with the lower housing 804 and the cogs 810, 812 removed. As can be seen therein, there is a spring 816 located in a groove 818 which is situated radially outward of where the first cog 810 would be, if shown. The spring 816 serves to bias the dial 608 back to its zero position when it is not being actuated. There is a peg 820 which extends rearwardly from the upper position marker 614 (which is on the front surface of the dial 608). This can also be seen in FIG. 7(e). The peg 820 is rotatable within an arc-shaped notch 822, which is comprised within the groove 818 and is limited to +/−60 degrees from the zero position. When the user moves the upper position marker 614 in order to actuate the dial 608 from the front, the peg 820 (at the rear) moves within the notch 822 and also compresses the spring 816. The notch 822 ensures that the peg 820 (and thus the upper position marker 614) cannot move more than +/−60 degrees. There is a claw 824 radially inward of the arc-shaped notch 822, which is in connection with the peg 820 and which extends axially rearwards, engaging with the first cog 810. The claw 824 thereby imparts movement to the first cog 810 when the dial is actuated by the user, via its front surface (for example, via the upper position marker 614). For example, the peg 820 and the claw 824 may be formed integrally with the so-called 'cap' which forms (at least part of) the outer surface of the dial 608. For example, they may be injection moulded.

FIG. 7(d) shows the cogs 810, 812, with the potentiometer 814. As shown therein, rotational movement of the first cog 810 will cause rotational movement of the second cog 812, which causes movement of the potentiometer. Potentiometer movements can be conveyed by the controller 600 to the therapeutic radiotherapy device, as control signals for the rotatable gantry or collimator.

As shown in FIG. 7(e), there is a so-called 'rolling bearing' 826 located between (in an axial or 'z' direction) the front surface of the dial 608 and the first cog 810 The rolling bearing 826 is provided to enable smooth rotation of the inner components of the dial, and to increase its durability and performance.

The inner components of the dial, such as the peg 820, groove 818, and rolling bearing 826 can be injection moulded from plastic or any other suitable material. This means that they are simple and efficient to manufacture.

Alternatively, they may be machined in metallic materials like steel or aluminium alloy.

The inner and outer (or front and rear) components of the dial 608 combine to form a compact and user-friendly actuator that can be used readily by a user to selectively control a gantry and a collimator on a therapeutic radiotherapy device. The movements required by the user are intuitive and comfortable, and the mechanisms for translating those movements into control signals for the device are streamlined and reliable.

The improved controller 600 described herein is, both as a whole and when considering its individual component features, highly user-friendly, as it provides the user with a comfortable and intuitive input means, for conveying control instructions to a LINAC or other therapeutic radiotherapy device. Because the user is able to make his or her input movements relative to a zero position, to which the dial 608 or table controller 620 is biased, he or she can quickly and easily learn how his or her movements translate to changes in physical attributes of the respective component of the device that is under control. The user therefore quickly learns how big or small an input is needed to change the speed of the relevant component to a desired extent and also how to change the component's rotational or linear (i.e. horizontal and/or vertical) position, by a desired amount. The user can then use this learning to guide subsequent control movements. Moreover, because there are separate actuators for the rotatable aspects of the device and the linearly moveable table, respectively, the risk of user confusion or error is reduced. That is; the controller 600 embodies the recognition that it is useful to save space by combining certain functions, relating to particular selected features, but that it is useful for other features to be separate therefrom.

The physical motions needed for actuating the most frequently-required actuators, such as the dial 608, table controller 620, enable bar 630 and panel shift controls, are comfortable for the user, requiring relatively small movements. Moreover, the movements required are substantially in the same plane as the plane of the user input surface 602 of the controller 600, on which other control means such as buttons will be located and on which the user's thumb would naturally rest when holding the controller 600, or on the side of the controller 600, where the user will naturally be gripping or cupping the controller 600, during use. The user will therefore be able to comfortably move his or her finger or thumb readily between the various actuators on the user input surface 602, and between actuating the actuators and merely holding the controller 600 or resting his or her hand on the surface of the controller 600. This is highly advantageous, particularly for users who may be seeing many patients, one after another, and therefore may need to use the controller for long periods of time, and/or repeatedly throughout the day.

By providing this easy-to-learn and intuitive control means, the controller enables the user to make more accurate changes to the speed and positioning of the moving components of the therapeutic radiotherapy device, which will increase the effectiveness of the radiotherapy for treating the patient's target region and help to avoid damage to otherwise healthy tissue and avoid collision between rotational parts and other static objects. It also has the effect of increasing the speed of radiotherapy, thereby improving patient throughput and improving overall experience for individual patients. This could also lead to cost savings, if the device is used more efficiently. The improved controller also increases the speed and facility with which a new or infrequent user of the device can understand, learn and retain how to use it; which limits the risk of user error or inaccuracy and also increases the usefulness of the therapeutic radiotherapy device to the hospital or other facility where it is used, because it makes the device readily useable by a greater number of users.

The control embodies intelligent and efficient recognitions, regarding what functions a user requires from a handheld controller of a Linac device, and which functions are (and are not) likely to be needed simultaneously. This has enabled the controller to be provided in a compact fashion—and to be provided as a single handheld device for controlling operation of a therapeutic radiotherapy device, as opposed to needing multiple handheld devices, as has previously been the case.

User Interface Module (UIM)

It is commonplace to provide a static User Interface Module (UIM) on a Linac or other therapeutic radiotherapy device, to work in conjunction with a set of hand held controllers. In fact, clinical workflows can be done with the hand held controller alone if user prefers to do so. But the UIM can be useful, for example to enable hands free operation if the user needed to use his or her hands temporarily to, for example, adjust the patient's position manually. In some arrangements, the UIM will be configured to provide more finely tuned control of certain components of the device, than the hand held controller would be. However, in some cases—for example when the patient table is at certain positions—the UIM may be difficult or impossible for the user to access, in which case(s) the user could rely solely on the handheld controller, at least temporarily.

In this case, the UIM works in conjunction with a single handheld controller 600, which is detailed above. The improved controller 600 is configured to work in conjunction with a machine-based UIM 700, such as the one shown in FIG. 6 herein.

The UIM 700 is located on the body of the Linac device—and so will not be moveable. In this arrangement, two identical UIM's 700 are provided, one either side of the body of the machine (i.e. mirrored about the longitudinal horizontal axis) so that the user may use a UIM 700 when located on either side of the machine. But in other arrangements, there may be more than two UIM's or just one UIM provided.

The UIM 700 includes various control buttons. For example, it comprises first 702 and second 704 controllers, that can be used to control, respectively, vertical and horizontal movement of the 'table' on which a patient is located for radiotherapy. It also provides a table ASU button 706, for Automatic Setup of the patient table. It also comprises longitudinal 708 and lateral 710 brake releases, for disengaging the corresponding clutches which connect the motor and the driving mechanism and instead enable manual movement of the patient table.

The UIM 700 also comprises an emergency 'stop motors' button 712 and a motors reset button 714.

Generally speaking, the UIM 700 can be used for initially setting up and moving the patient table, and for emergency measures such as stopping the motors of the device in the event of an emergency. But the UIM is not used for controlling the application of the radiation. This is done by a separate means (see below). A user may choose to use the UIM for configuring the gantry and/or the collimator for the application of radiation for therapeutic radiotherapy. However, when using the UIM the user is obliged to remain at a fixed location, which will not always be possible or helpful.

As discussed in detail above, rather than relying on the UIM at all times, the user may instead choose to use the improved controller 600 for controlling the rotatable aspects of the Linac's operation—and also for controlling patient table position, and panel position and so on. An advantage of the controller 600, over the UIM, is that it enables the user to be generally free to move around, and not to be located at the machine, when radiotherapy is being applied. Because the controller 600 has been intelligently designed, to provide all the functionality that the user is likely to need during the course of a radiotherapy treatment session, the user would not need to switch between using the handheld controller 600 and the UIM 700. Therefore the controller 600 provides a very user friendly control means. This has a knock-on effect of providing a more positive patient experience and enabling more efficient and streamline treatment, using the controlled therapeutic radiotherapy device.

There is another physical user interface that interacts with the Linac device, called Function Key Pad (FKP) (not shown in the figures). The FKP is usually located in situ in the control room and is the only place that user can initiate the radiation, for the therapeutic radiotherapy treatment.

Variations

It will be appreciated that the relative location of different features of the user-input surface of the controller can be varied, whilst still providing the control improvements described above in relation to the particular arrangement shown in FIG. 5 herein. Moreover, the precise number, size, shape and spacing of certain features can be changed. For example, the cross-shaped actuator could be omitted or replaced by a different type of actuator or button, or there could be more than one cross-shaped actuator. Or, for example, the table controller may take a form other than a 4 way slider.

In the arrangement described, the dial is spring biased but any other suitable type of bias may be used, to return the dial to a 'zero' or neutral resting position between actuations. Similarly, the resting position of the dial need not be at 12 o'clock or 0°. Similarly, the table controller may be biased in a different manner to the precise form described above in relation to FIG. 5. The particular inner (or rear) components of the dial may be varied, as compared to those described above in relation to FIG. 7.

Any section headings used herein are merely for organisational purposes. They are not to be construed as limiting or dividing the subject matter disclosed in the application as a whole.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A controller for a radiotherapy device configured to provide therapeutic radiation to a patient via a source of therapeutic radiation, the radiotherapy device comprising:

a first rotatable member, the rotation of which alters a physical attribute of the therapeutic radiation provided; and a patient support member linearly moveable in at least one of a longitudinal direction or a lateral direction;

wherein the controller comprises:

a first rotatable actuator configurable for controlling a movement of the first rotatable member, wherein the first rotatable actuator is biased towards a rest position and wherein the controller is arranged for detection of a user actuation of the first rotatable actuator away from the rest position; and a second actuator configurable for controlling a movement of the patient support member.

2. The controller of claim 1, wherein a movement of the first rotatable actuator away from the rest position can be used to control a property of the movement of the first rotatable member.

3. The controller of claim 1, wherein the controller includes a potentiometer configured to convey a control signal to the radiotherapy device, based on the movement of the first rotatable actuator away from the rest position.

4. The controller of claim 1, wherein the first rotatable actuator is provided on a user input surface of the controller and is configured so that a user actuation of the first rotatable actuator can be provided in substantially a same plane as the user input surface.

5. The controller of claim 2, wherein a size of a movement of the first rotatable actuator away from the rest position, as a result of an actuation by the user, is proportional to a size of a resultant change in the property of the movement of the first rotatable member, which is being controlled.

6. The controller of claim 1, wherein a direction of the movement of the first rotatable actuator away from the rest position, as a result of an actuation by the user, will determine a direction of a resultant change in position of the first rotatable member.

7. The controller of claim 1, wherein the first rotatable actuator is spring biased to a rest position.

8. The controller of claim 1, wherein the radiotherapy device further comprises:

a second rotatable member.

9. The controller of claim 8, wherein the controller is arranged for selective control of movement of the first rotatable member and the second rotatable member, using the first rotatable actuator.

10. The controller of claim 9, wherein the selective control enables the first rotatable actuator to be used to control either the first rotatable member or the second rotatable member, in accordance with a user selection.

11. The controller of claim 10, further comprising a selection component configured to accept an input of a user selection to determine which rotatable member to control.

12. The controller of claim 1, wherein the second actuator is configured to be actuated using substantially linear user movements.

13. A radiotherapy device configured to provide therapeutic radiation to a patient via a source of therapeutic radiation the radiotherapy device comprising:

a first rotatable member, the rotation of which alters a physical attribute of the therapeutic radiation provided; and a patient support member, which is linearly moveable in at least one of a longitudinal direction and a lateral direction;

wherein the radiotherapy device is configured for control by a controller comprising a first rotatable actuator configured to control a movement of the first rotatable member and a second actuator configured to control a movement of the patient support member, and wherein the first rotatable actuator is biased towards a rest position, and wherein the controller is arranged for detection of a user actuation of the first rotatable actuator away from the rest position.

14. The radiotherapy device of claim 13, wherein the controller includes a potentiometer configured to convey for conveying a control signal to the radiotherapy device, based on the movement of the first rotatable actuator away from the rest position.

15. A system to provide therapeutic radiation to a patient via a source of therapeutic radiation, the system comprising:
   a radiotherapy device; and
   a controller communicatively coupled to the radiotherapy device, wherein the radiotherapy device includes:
      a first rotatable member, the rotation of which alters a physical attribute of the therapeutic radiation provide;
      a patient support member linearly movable in at least one of a longitudinal direction or a lateral direction; and
      a second rotatable member;
   wherein the controller includes:
      a first rotatable actuator configurable for controlling a movement of the first rotatable member, wherein the first rotatable actuator is biased towards a rest position, and wherein the controller is configured for detection of a user actuation of the first rotatable actuator away from the rest position;
      a second actuator configurable for controlling a movement of the patient support member; and
      a potentiometer configured to convey a control signal to the radiotherapy device, based on the movement of the first rotatable actuator away from a rest position.

16. The system of claim 15, wherein the first rotatable actuator is located on a user input surface of the controller and is configured so that the user actuation of the first rotatable actuator can be provided in substantially a same plane as the user input surface.

17. The system of claim 15, wherein an amount of a movement of the first rotatable actuator away from the rest position, as a result of the actuation by the user, is proportional to a size of a resultant change in a property of the movement of the first rotatable member, which is being controlled.

18. The system of claim 17, wherein a direction of the movement of the first rotatable actuator away from the rest position, as a result of an actuation by the user, will determine a direction of a resultant change in position of the first rotatable member.

* * * * *